United States Patent [19]

Bellon et al.

[11] Patent Number: 5,461,163
[45] Date of Patent: * Oct. 24, 1995

[54] **SYNTHESIS AND PURIFICATION OF [R-(R*,R*)]-5-[2-[5-(3-CHLORO-PHENYL)-2-OXO-3-OXAZOLIDINYL]-PROPYL]-1,-3-BENZODIOZOLE-2,2-DICARBOXYLIC ACID DIMETHYL ESTER**

[75] Inventors: Christine P. Bellon, Hamden, Conn.; David M. Blum, Upper Saddle River, N.J.; William T. Cain, Nanuet, N.Y.

[73] Assignee: American Cyanamid Company, Wayne, N.J.

[*] Notice: The portion of the term of this patent subsequent to Sep. 29, 2009 has been disclaimed.

[21] Appl. No.: 254,806

[22] Filed: Jun. 6, 1994

[51] Int. Cl.⁶ .................................................. C07D 317/44
[52] U.S. Cl. .................................................. 548/229
[58] Field of Search .................................................. 548/229

[56] References Cited

U.S. PATENT DOCUMENTS

| | | | |
|---|---|---|---|
| 5,061,727 | 5/1990 | Bloom et al. | 548/229 |
| 5,106,867 | 4/1992 | Bloom et al. | 514/376 |
| 5,151,439 | 9/1992 | Bloom et al. | 548/229 |

OTHER PUBLICATIONS

Bloom et al. Chem. Abstr. vol. 117 entry 131102 (1992).

*Primary Examiner*—Donald G. Daus
*Attorney, Agent, or Firm*—H. G. Jackson; R. F. Boswell, Jr.

[57] ABSTRACT

The invention relates to a process improvement for making [R-(R*,R*)]-5-[2-[5-(3-chlorophenyl)-2-oxo-3-oxazolidinyl] propyl]-1,3-benzodioxole-2,2-dicarboxylic acid dimethyl ester an intermediate used in the synthesis of beta-3 agonist, [R-(R*,R*)]-5-[2-[5-(3-chlorophenyl)-2-hydroxyethyl] amino] propyl] -1,3-benzodioxole-2,2-dicarboxylic acid disodium salt.

2 Claims, No Drawings

SYNTHESIS AND PURIFICATION OF [R-(R*,R*)]-5-[2-[5-(3-CHLORO-PHENYL)-2-OXO-3-OXAZOLIDINYL]-PROPYL]-1,-3-BENZODIOZOLE-2,2-DICARBOXYLIC ACID DIMETHYL ESTER

FIELD OF THE INVENTION

The invention relates to a process improvement for making [R-(R*,R*)]-5-[2-[5-(3-chlorophenyl)-2-oxo-3-oxazolidinyl] propyl]-1,3-benzodioxole-2,2-dicarboxylic acid dimethyl ester an intermediate used in the synthesis of beta-3 agonist, [R-(R*,R*)]-5-[2-[5-(3-chlorophenyl)-2-hydroxyethyl]amino]propyl]-1,3-benzodioxole- 2,2-dicarboxylic acid disodium salt.

BACKGROUND OF THE INVENTION

U.S. Pat. No. 5,061,727, teaches the making of [R-(R*, R*)]-5-[2-[5-(3-chlorophenyl)-2-oxo-3-oxazolidinyl] propyl]-1,3-benzodioxole-2,2-dicarboxylic acid diethyl ester, an oil which must be purified by a lengthy chromatography. The purity of the diethyl ester oil obtained is approximately 95% by area.

SUMMARY OF THE INVENTION

The invention involves making the dimethylester of [R(R*,R*)]-5-[2-[5-(3-chlorophenyl)- 2-oxo-3-oxazolidinyl]propyl]-1,3-benzodioxole-2,2-dicarbocylic acid. The modification making the dimethyl ester rather than the diethyl ester, has the unforeseen benefit of producing a crystalline product and the product so produced is 99% pure by area. The time required to make and purify the dimethyl ester is less, by a factor of 20, than the time required for the diethyl ester.

DESCRIPTION OF THE INVENTION

Scheme 1

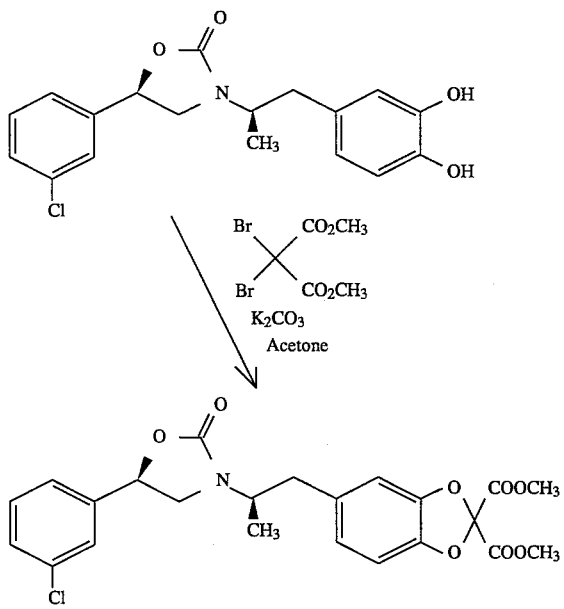

According to Scheme 1, [R-(R*,R*)]-5-(3-chlorophenyl)-3-[2-((3,4-dihydroxyphenyl)-1-methylethyl]- 2-oxazolidinone, prepared by procedures described in U.S. Pat. No. 5,061,727, is treated with dimethyl dibromomalonate in acetone. The reaction is cooled to 10° C. and potassium carbonate is added. The reaction is stirred and maintained at between 20°–25° C. overnight. Hydrated magnesium silicate is added and the reaction mixture is diluted with toluene, filtered and concentrated in vacuo to approximately half volume. The solution is diluted with methyl alcohol and concentrated in vacuo. This procedure is repeated 2 times. The residue is dissolved in methyl alcohol, stirred and allowed to crystallize. The product is collected and dried to give the desired product as white crystals.

The unexpected crystallinity of the dimethyl ester is a notable advantage. Large scale preparations, pilot plant etc., are much easier to handle if the product is in crystalline form. The need for large scale chromatography, such as that required for the purification of the diethyl ester, is not amenable to pilot plant runs.

By using crystallization of the dimethyl ester, instead of chromatography of the diethyl ester, the time required to purify the intermediate is reduced by a factor of 20, the volumes of solvents are reduced by a factor of 4 and the product is purer. Below is a composite Table of the differences and advantages of making and using the dimethyl ester as an intermediate in the synthesis of [R-(R*,R*)]-5-[2-[5-(3-chlorophenyl)- 2-hydroxyethyl]amino]propyl]-1,3-benzodioxole- 2,2-dicarbocylic acid disodium salt.

|  | Diethyl ester | Dimethyl ester |
| --- | --- | --- |
| Best solvents | Tetrahydrofuran, toluene, acetonitrile | Acetone |
| Reaction Time | 4 hours | 24 hours |
| Method of Purification | Chromatography | crystallization |
| Typical purity | 95% area | 99% area |
| Reaction Yield (after purification) | 65% | 65% |
| Time required to purify 25 kg | 17 days | 1 day |
| Amount of solvent required to purify 25 kg | 2100 liter | 150 liter |

This invention will be described in greater detail in conjunction with the following example.

EXAMPLE 1

[R-(R*,R*)]-5-[2-[2-(-chlorophenyl)-2-oxo-3-oxazolidinyl] propyl]-1,3-benzodioxole-2,2-dicarboxylic acid dimethyl ester Four hundred grams of [R-(R*,R*)]-5-(3-chlorophenyl)-3-[2-(3,4-dihydroxyphenyl)-1-methylethyl- 2-oxazolidione and 500 g of dimethyl dibromomalonate are dissolved in 3520 ml of acetone and cooled to 10° C. To the solution is added 138 g of potassium carbonate and the temperature is maintained between 20°–25° C. overnight with stirring. Thin layer chromatography indicates the absence of starting material. Two hundred grams of hydrous magnesium silica and 3500 ml of toluene is added and the reaction is filtered and washed with 5000 ml of toluene. The filtrate is concentrated to approximately 3000 ml. To facilitate the handling, the concentrate is divided into 2 equal portions. Each 1.5 L concentrate is diluted with 3.0 L of methyl alcohol, concentrated in vacuo, redissolved in 1.0 L of methyl alcohol, stirred and allowed to crystallize. The product is collected, washed and dried to give 170 g of a white crystalline solid, mp 113°–115° C.

Purity= 99.2% Wt/Wt
Yield= 62%.
Analysis calculated for $C_{23}H_{22}ClNO_8$:
Theory: C=58.05; H=4.66; N=2.94; Cl=7.45
Found: C=57.86; H=4.54; N=2.90; Cl=7.47
IR(KBr): 1949, 1881, 1784, 1770, 1737, 1496 cm$^{-1}$.
$^1$HNMR(CDCl$_3$): δ7.3–6.6(m, 7H); 5.38(dd,1H, J=6.3 and 8.9 Hz); 4.23(m, 1H); 3.91(s,3H); 3.90(s,3H); 3.85(t,1H, J=8.8 Hz); 3.27(dd, 1H, J=6.3 and 8.5 Hz); 2.73 (d,2H, J=7.7 Hz); 1.24(d,3H, J=6.8 Hz).
$^{13}$C NMR(CDCl$_3$): ppm 17.42, 39.72, 47.82, 49.93, 53.67, 73.34, 105.36, 108,82, 109.57, 122.87, 123.30, 124.43, 128.69, 130.16, 132.58, 134.54, 141.05, 144.48, 145.94, 156.75, 163.78.

We claim:

1. A process for making a compound of the formula 1:

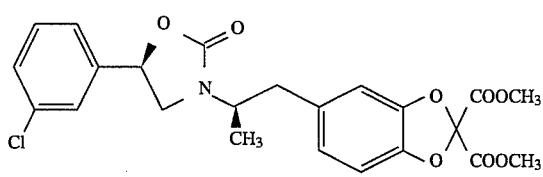

which comprises:

a) reacting, at 10° C., [R-[R*,R*]-5-(3-chlorophenyl)-3-[2-((3,4-dihydroxyphenyl)- 1-methyl-ethyl]-2-oxazolidinone:

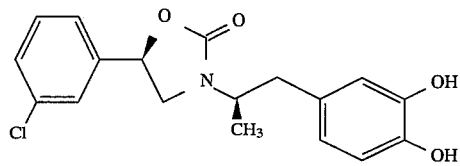

with dimethyl dibromomalonate in acetone, adding potassium carbonate and maintaining the temperature at 20°–25° C. until the dihydroxy reactant is consumed;

b) addition of hydrated magnesium silicate in toluene followed by removal of toluene; and c) crystallization of the product from methanol to obtain the formula 1 compound in crystalline form.

2. A crystalline compound of the formula:

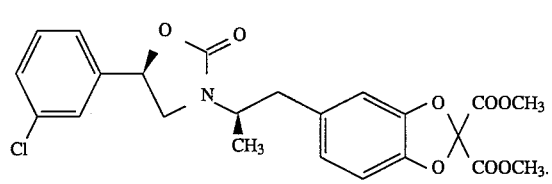

* * * * *